United States Patent [19]

Marchal et al.

[11] Patent Number: 5,599,541
[45] Date of Patent: Feb. 4, 1997

[54] **PEPTIDE SEQUENCE CAPABLE OF INDUCING A DELAYED-TYPE HYPERSENSITIVITY REACTION IN THE PRESENCE OF LIVING BACTERIA OF THE *MYCOBACTERIUM TUBERCULOSIS* COMPLEX AND ITS APPLICATIONS**

[75] Inventors: Gilles Marchal, Ivry S/Seine; Félix Romain, Fontenay Les Briis, both of France

[73] Assignee: Institut Pasteur, Paris Cedex, France

[21] Appl. No.: 302,771

[22] PCT Filed: Mar. 17, 1993

[86] PCT No.: PCT/FR93/00268

§ 371 Date: Oct. 17, 1994

§ 102(e) Date: Oct. 17, 1994

[87] PCT Pub. No.: WO93/19093

PCT Pub. Date: Sep. 30, 1993

[30] Foreign Application Priority Data

Mar. 19, 1992 [FR] France .................................... 92 03286

[51] Int. Cl.$^6$ .......................... A61K 39/02; A61K 37/04; C07K 1/00
[52] U.S. Cl. .................................... 424/190.1; 424/248.1; 530/350; 436/57; 435/35
[58] Field of Search .............................. 424/190.1, 248.1; 530/350, 412, 416; 436/57, 808; 435/35, 975

[56] References Cited

U.S. PATENT DOCUMENTS 4,619,828 10/1986 Gordon ...................................... 424/92
4,876,193 10/1989 Gottlieb ..................................... 435/29

OTHER PUBLICATIONS

Sevier et al. Clin. Chem. (1981) 27(11): 1797–1806.
Damle et al. J. Immunol. (1984) 132(2): 644–650.
DeBruyn et al. Infection & Immunity (1987) 55(1): 245–252.

*Primary Examiner*—James C. Housel
*Assistant Examiner*—Jennifer Shaver
*Attorney, Agent, or Firm*—Oblon, Spivak, McClelland, Maier & Neustadt, P.C.

[57] ABSTRACT

Peptide sequence capable of initiating delayed hypersensitivity reactions of different intensity in the presence of living bacteria as opposed to dead bacteria of the *Mycobacterium tuberculosis* complex. The sequence is characterized in that it comprises no more than 0.5% by weight of tyrosine, phenylalanine, methionine, histidine, arginine and cysteine amino acids. The invention also concerns the diagnostic and therapeutic applications of a peptide or protein comprising said sequence.

15 Claims, 7 Drawing Sheets

FIG. 4

FIG. 6

PEPTIDE SEQUENCE CAPABLE OF INDUCING A DELAYED-TYPE HYPERSENSITIVITY REACTION IN THE PRESENCE OF LIVING BACTERIA OF THE *MYCOBACTERIUM TUBERCULOSIS* COMPLEX AND ITS APPLICATIONS

BACKGROUND OF THE INVENTION

1. Field of the Invention

The present invention relates to a new antigenic protein capable of causing delayed hypersensitivity reactions of different intensity in the presence of living or dead bacteria of the *Mycobacterium tuberculosis* complex, its diagnostic and therapeutic applications especially as vaccine.

This *Mycobacterium tuberculosis* complex comprises four species: *Mycobacterium tuberculosis, Mycobacterium bovis, Mycobacterium africanum, Mycobacterium microti* (*le Minor et Veron; bacteriologie Madicale* 1990, 2nd ed. p. 1966).

2. Discussion of the Background

The delayed-type hypersensitivity reaction to tuberculin is used commonly as means of diagnosing tuberculosis. This tuberculin challenge is particularly used as diagnostic means in the United States and in the Netherlands, countries where BCG vaccination does not or no longer exists. A recent development (1990) by the American Thoracic Society recommends in particular the use of this diagnostic test and specifies its limits for the national campaign for the total eradication of tuberculosis which is being put in place in the United States. For France, the medical practice is a little different because of the wide use of BCG and the still relatively high frequency of tuberculosis. The reaction to tuberculin is used to monitor secondary sensitization to the vaccination and also to provide arguments in favor of the existence of a tubercular infection. This diagnostic indication is based on the clear increase in the intensity of the reaction in a given subject or on the very high intensity of the reaction. But this quantitative notion is difficult to assess accurately when the tuberculin reactions are performed and/or read by different people.

In fact, the delayed-type hypersensitivity skin reaction to tuberculin does not currently allow sick subjects having a developing tuberculosis to be differentiated with certainty from previously sensitized subjects. Indeed, subjects carrying numerous living bacilli (patients suffering from tuberculosis or recently vaccinated subjects) may present the same skin reactivity to tuberculin as subjects who have been previously sensitized by a primary infection cured spontaneously or having suffered a tuberculosis which is now cured.

SUMMARY OF THE INVENTION

The inventors have isolated and purified a new protein called LIP-DTH from BCG culture medium which is found to be capable of causing a delayed-type hypersensitivity in guinea pigs with no consanguinity which are immunized with living bacilli (BCG), without in contrast causing a substantial reaction in guinea pigs immunized with dead bacilli (BCG).

This difference in reactivity was also observed in mice from two different lines (C57Bl/6 and C3H/He).

Likewise, guinea pigs and mice having received virulent tuberculosis bacilli (strain H37Rv) show a reactivity towards this protein which is identical to the reaction observed in animals having received living BCG.

A study of the amino acid composition of LIP-DTH revealed a protein having a very unusual amino acid composition, numerous amino acids such as tyrosine, phenylalanine, methionine, histidine, arginine and cysteine being absent or being present in undetectable quantities.

The subject of the present invention is thus a peptide sequence capable of initiating delayed hypersensitivity reactions of different intensity in the presence of living bacteria as opposed to dead bacteria of the *Mycobacterium tuberculosis* complex, characterized in that it contains not more than 0.5% by weight of the amino acids tyrosine, phenylalanine, methionine, histidine, arginine and cysteine.

The subject of the invention is also a peptide or a protein capable of inducing an immune response in the human or animal host to which it is administered, having peptide sequence as defined above and characterized in that its overall amino acid composition, expressed in percentage relative to the total molecular weight is essentially the following:

Asp/Ash 1.2
Thr 12.2
Set: 2.5
Glu/Gln: 11.5
Gly: 7.7
Ala: 8.9
Val: 9.8
Ile: 2.8
Leu: 1.8
Lys: 1.6
Pro: 40.0

The protein according to the invention can be obtained from BCG culture supernatant by the purification steps consisting in:

(a) a filtration on molecular sieve, and, (b) an ion-exchange chromatography on DEAE and (c) a reversed-phase chromatography.

The protein according to the invention induces a delayed-type hypersensitivity which is very intense in the presence of living bacilli and much less intense in the presence of dead bacilli.

The "tuberculin" activity of this protein is thus equivalent to about 415,000 International Tuberculin Units (ITU) per mg in guinea pigs immunized with living bacilli, and to 3000 ITU per mg in guinea pigs immunized with dead bacilli.

The subject of the present invention is therefore also a diagnostic composition characterized in that it comprises a protein according to the invention.

This composition is used to detect the presence of virulent bacteria especially for the in vitro and in vivo diagnosis of tuberculosis in man and in animals (mammals).

BRIEF DESCRIPTION OF THE DRAWINGS

For the in vivo diagnosis of tuberculosis, the composition comprises for example 1 ng to 1 µg of protein/ml. Advantageously, the diagnostic composition also comprises a saline solution containing a surface-active agent intended to avoid the adhesion of the antigenic protein to the packaging container or to the syringe used for the injection. A particularly preferred excipient for the composition according to the invention comprises:

75 g/l of glycocol 20 g/l of NaCl 2.375 ml/l of 35 to 10% Brij 30 ml/l of 1M Na$_2$HPO$_4$ pH 7.1 balance: apyrogenic distilled water, the excipient being autoclaved for 20 min at 120° C.

The composition is preferably administered intradermally in an amount of 0.1 ml of solution containing a dose of 2 ITU (international tuberculin units) using a tuberculin syringe provided with a 4/10 th needle on the front face of the forearm according to the method used for the tuberculin test.

Other routes of administration such as the application of a ring, a scarification or application via the skin can also be envisaged.

After a period of about 48 to 96 hours, according to the species, (about 48 to 72 hours in man), the appearance of a local reaction resulting in an erythema and/or an induration is examined. The appearance of such a reaction makes it possible to establish the diagnosis of a sensitization using an immunological reaction having as origin T lymphocytes sensitized by antigens of bacteria of the *Mycobacterium tuberculosis* complex.

The injection of the LIP-DTH protein, preferably intradermally under the same conditions as an injection of tuberculin makes it possible, for low concentrations of this protein, to detect a tuberculin-type reaction only in subjects carrying living bacilli, that is to say subjects recently infected, patients having tuberculosis or recently vaccinated subjects, and not in the control subjects, nevertheless sensitized towards the conventional tuberculin.

The subject of the present invention is also an immunogenic composition comprising a peptide or a protein according to the invention, which is intended to allow a stimulation of the immune system in order to obtain a B- or T-type response in a human or animal subject (mammal) so as to protect it against a subsequent infection by bacteria of the *Mycobacterium tuberculosis* complex.

Advantageously, the immunogenic composition according to the invention comprises as active ingredient 1 ng to 1 mg of LIP-DTH protein.

The route of administration comprises all those conventionally used for vaccines, for example the oral, intravenous, intradermal, intramuscular, subcutaneous, aerosol or sublingual routes.

This composition may or may not comprise an adjuvant having immunostimulant properties, such as inorganic salts, for example aluminum hydroxide, hydrophobic compounds or surfactants, for example incomplete Freund's adjuvant in animals, squalene or liposomes, synthetic polynucleotides, microorganisms or components of microorganisms, for example murabutide, synthetic artificial molecules, or alternatively cytokines, for example α-, β- or γ-interferons or natural interleukins or interleukins obtained by expression of recombinant hosts.

The immunogenic composition according to the invention can also be used as desensitization composition.

Some authors consider indeed that the disease caused by bacteria of the *Mycobacterium tuberculosis* complex may, in part, be due to the massive T lymphocyte immune response in response to the stimulation by the antigens of these bacteria.

It may therefore be important in certain cases to desensitize a human or animal subject by administering thereto at repeated intervals, for example of 8 to 15 days a composition as described above.

Trials carried out with the LIP-DTH protein have shown a very high intensity of the delayed-type hypersensitivity reaction, including with small quantities of injected living bacteria (of the order of $2\times10^3$) when the challenge was performed more than 20 days after the immunization. Moreover, the immune response induced by the LIP-DTH protein is a "pure" thymodependent response, the antibody response towards this protein being very weak or zero during the immunization with living (or dead) bacteria as well as during the immunization with the purified protein.

These results lead to the LIP-DTH protein being proposed as molecule "carrying" epitopes towards which a T lymphocyte response is favored.

The subject of the invention is therefore also an immunogenic composition comprising a protein according to the invention onto which is added or attached an epitope against which a T-type response is desired.

This epitope may be of bacterial (for example mycobacteria), parasitic (for example Leishmania, Trypanosoma or Toxoplasma) or viral (Aids virus (HIV), Epstein-Bart virus or hepatitis B virus (HBV), origin.

Among the preferred epitopes, there may be mentioned the gag antigens and/or the nef antigen of HIV or all or part of the envelope 913 120 of HIV 1 or gp 140 of HIV 2, diphtheria toxin or fragments thereof, tetanus toxin, the HBS antigen of the HBV virus or alternatively the VP1 antigen of the polyomyelitis virus.

The epitope can be coupled to the carrier protein by means of bifunctional bridging agents such as glutaraldehyde, benzoquinone or N-bromosuccinimide, which are well known for their properties for coupling proteins to each other or such as hydrazide which permits the coupling of glycosylated residues to proteins.

The subject of the invention is also the use of an immunogenic composition according to the invention for the purposes of diagnosis in man or animals of a T lymphocyte response.

The subject of the invention is also the use of an immunogenic composition according to the invention in man or animals for the stimulation of the T lymphocytes, which is either general, or specific or directed against a particular epitope in the case where the protein according to the invention is coupled to an epitope as previously defined.

The subject of the invention is also an in vitro process for the detection of a T response against an infectious agent in a human or animal host, characterized in that it comprises the following steps:

culturing in an artificial medium mononuclear cells of the host containing varying concentrations of the peptide or of the protein, as previously defined, and detecting the activation of the mononuclear cells of the host.

To this end, mononuclear cells obtained from sensitized or non-sensitized subjects are cultured in a medium such as RPMI 1640 or MEM containing 2 to 20% homologous or heterologous serum at a concentration ranging from 10 to $10^6$ cells/ml, a medium containing varying concentrations of the peptide or of the protein as previously defined (1 ng to 10 μg/ml for example). Only the cells obtained from sensitized subjects will be activated for chosen concentrations of the peptide or of the protein. It will be possible to observe this activation by direct examination of the cells under a microscope (lymphoblastic transformation), high incorporation of radioactive precursors (thymidine, uridine and the like) by the presence, in the culture medium of different cytokines (IL2, $INF_\gamma$, and the like) or by the appearance on the surface of the cells of receptors for these cytokines.

Advantageously, the detection of the activation of the cells is performed by the detection of the γ-interferon released by the sensitized cells, by means of an enzymatic immunoassay using a monoclonal antibody.

The subject of the invention is also a diagnostic kit for the detection of a T response against an infectious agent in man or animals, characterized in that it comprises:

a culture medium for mononuclear cells, containing varying concentrations of the peptide or of the protein according to the invention, and means for detecting the activation of the mononuclear cells of a host.

Figure 1:
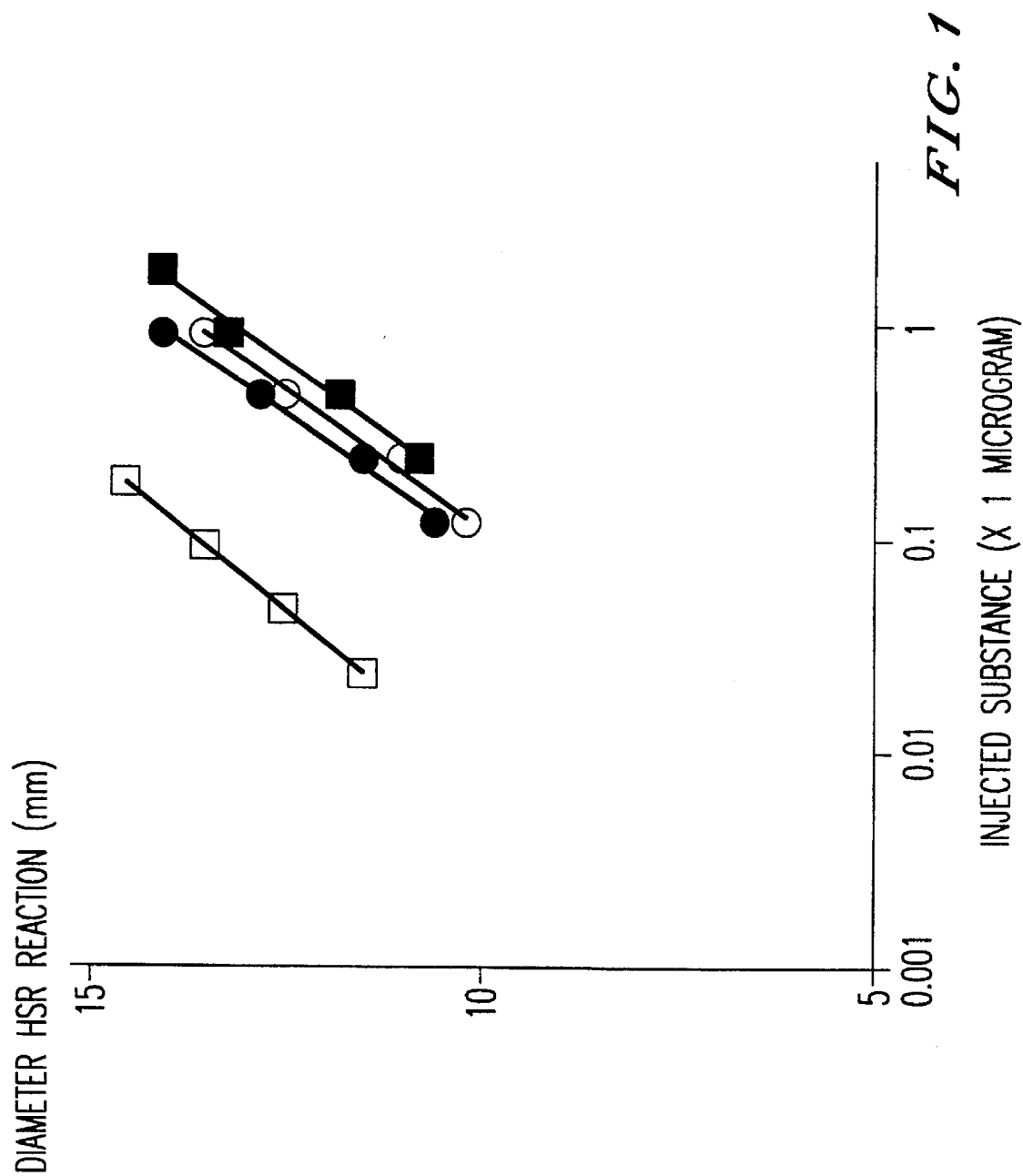
Figure 2:
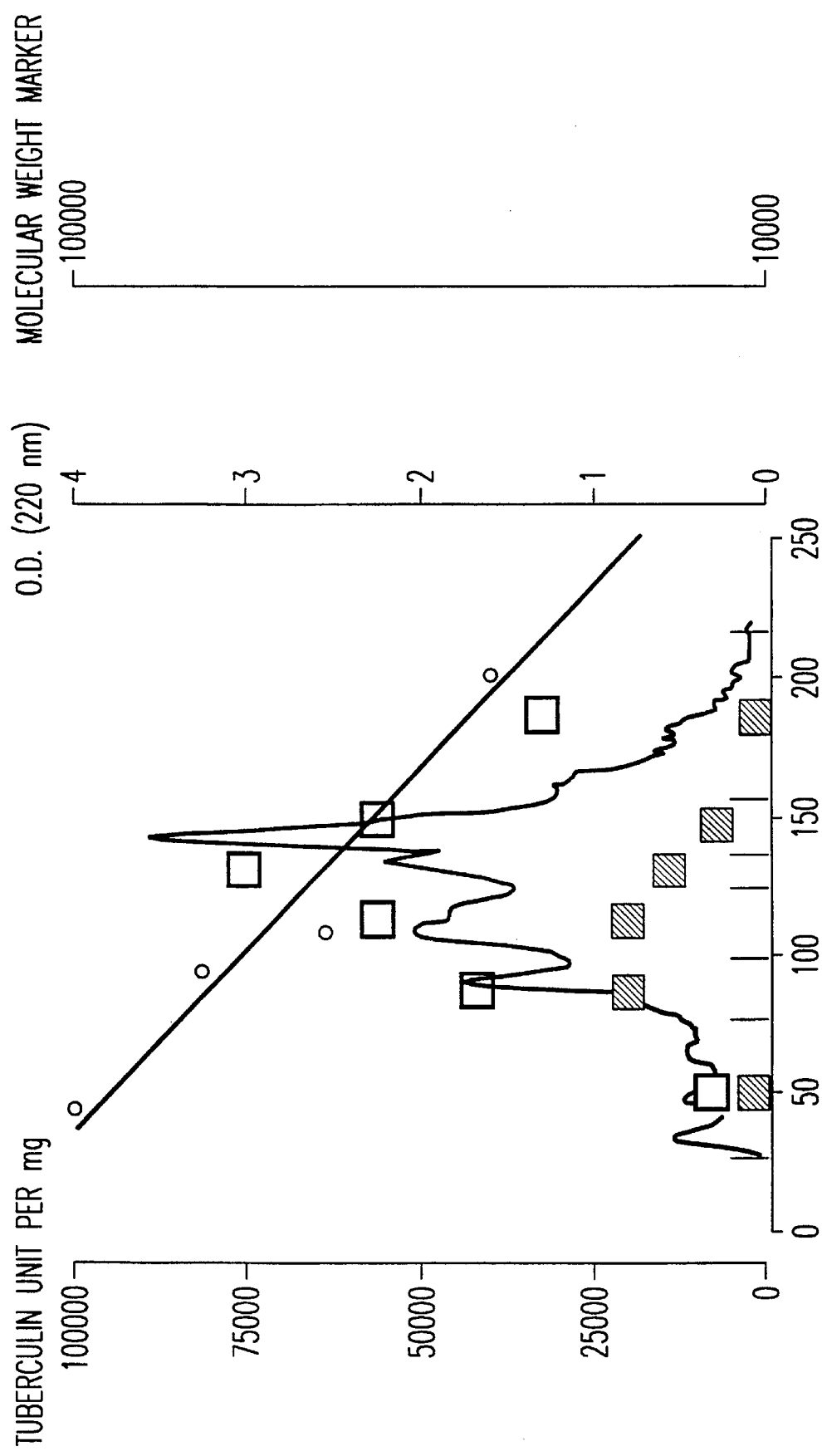
Figure 3:
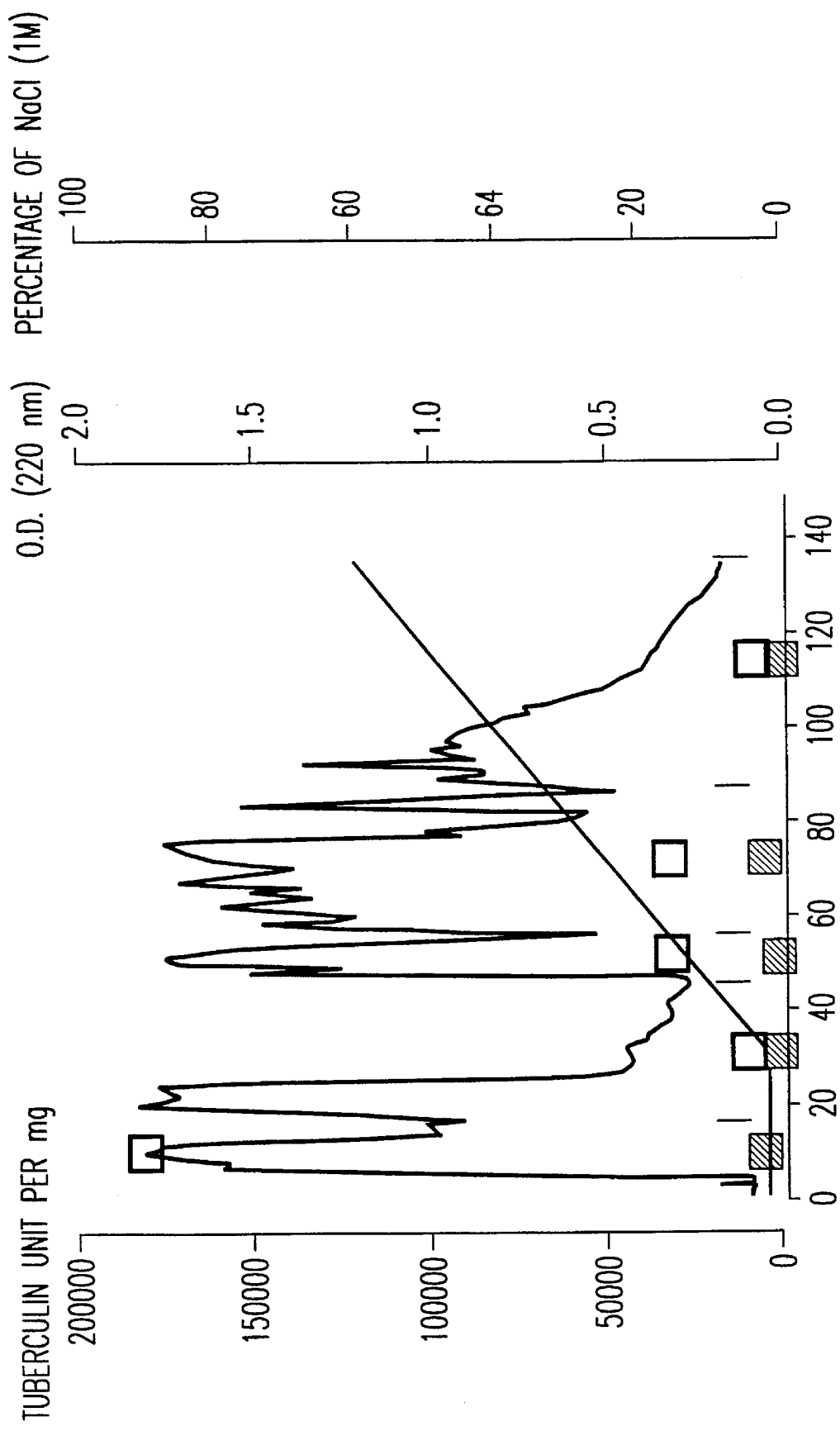
Figure 5:
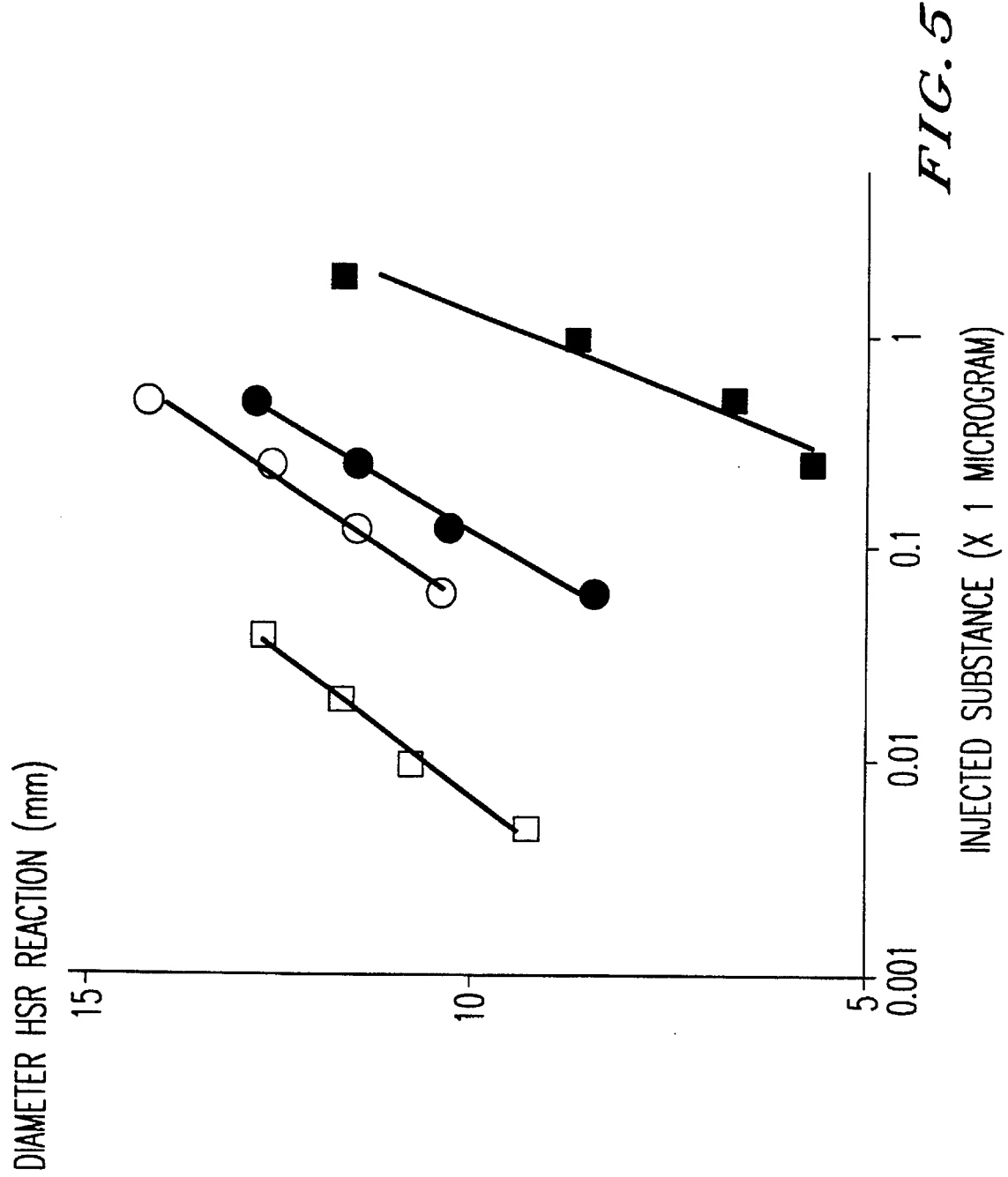

The purification of the LIP-DTH protein as well as its characteristics will be described in greater detail below with reference to the accompanying figures in which:

FIG. 1 represents the results of the HSR reactions in guinea pigs immunized with living bacteria (white symbols) or dead bacteria (black symbols) and tested with a standard PPD (Purified Protein Derivative) (circles) or the culture filtrate (squares);

FIG. 2 represents the results of molecular filtration of the substance present in the culture medium after 14 days of growth of the BCG and the HSR activity of the major fractions tested on guinea pigs immunized with living bacteria (white squares) and dead bacteria (black squares);

FIG. 3 represents the results of purification on a DEAE column of the molecules present in the fraction 4 obtained after gel filtration and the HSR activity of the major fractions tested on guinea pigs immunized with living bacteria (white squares) and dead bacteria (black squares);

Figure 4:
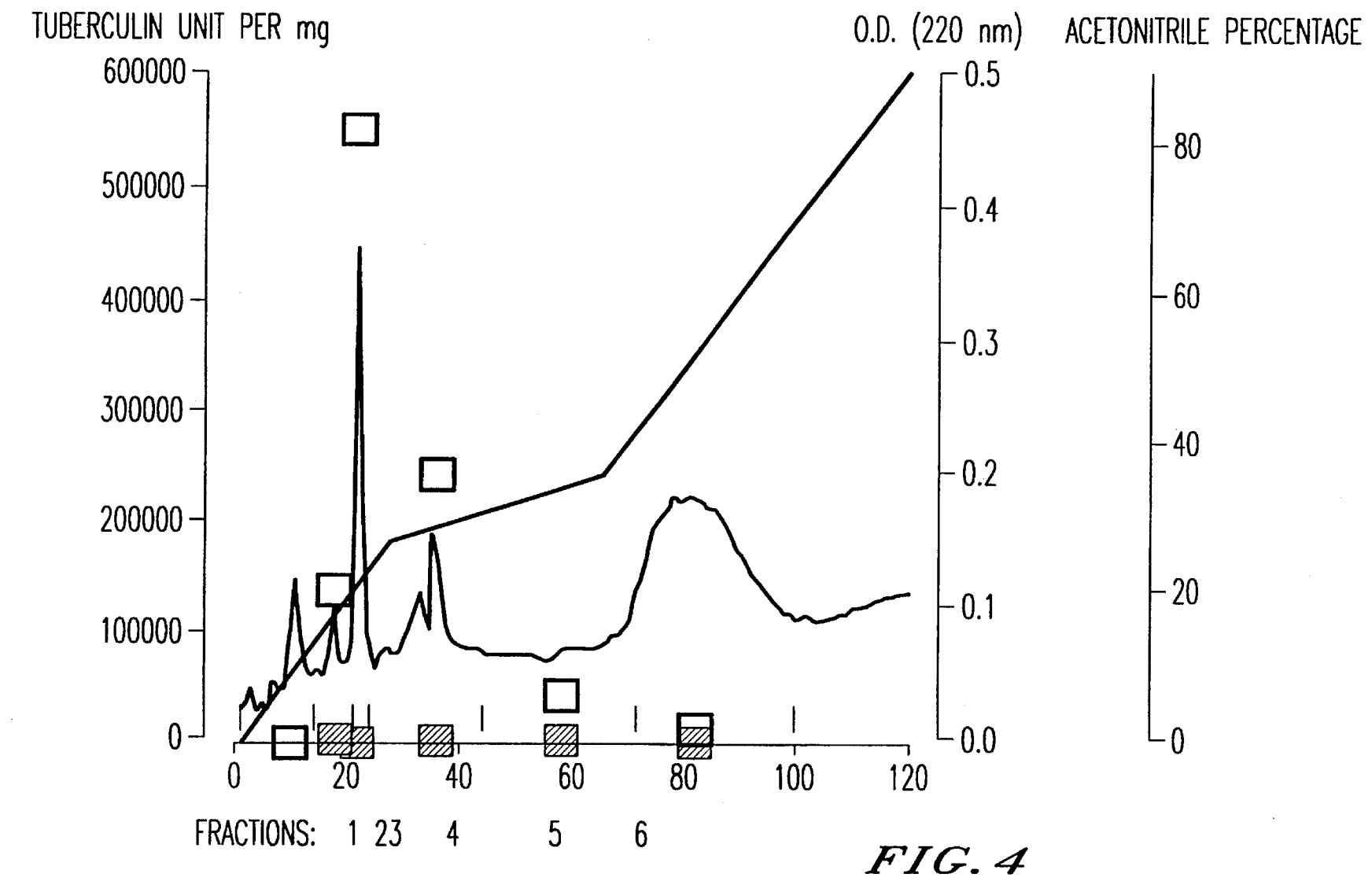

FIG. 4 represents the results of purification on a reversed-phase column of the molecules present in the fraction 1 of the separation on DEAE and the HSR activity of the major fractions tested on guinea pigs immunized with living bacteria (white squares) and dead bacteria (black squares);

FIG. 5 represents the results of the HSR activity of the major fractions tested on guinea pigs immunized with living bacteria (white squares) and dead bacteria (black squares) and tested with a standard PPD (Purified Protein Derivative) (circles) or fraction 3 of the reversed-phase chromatography step (squares);

Figure 6:
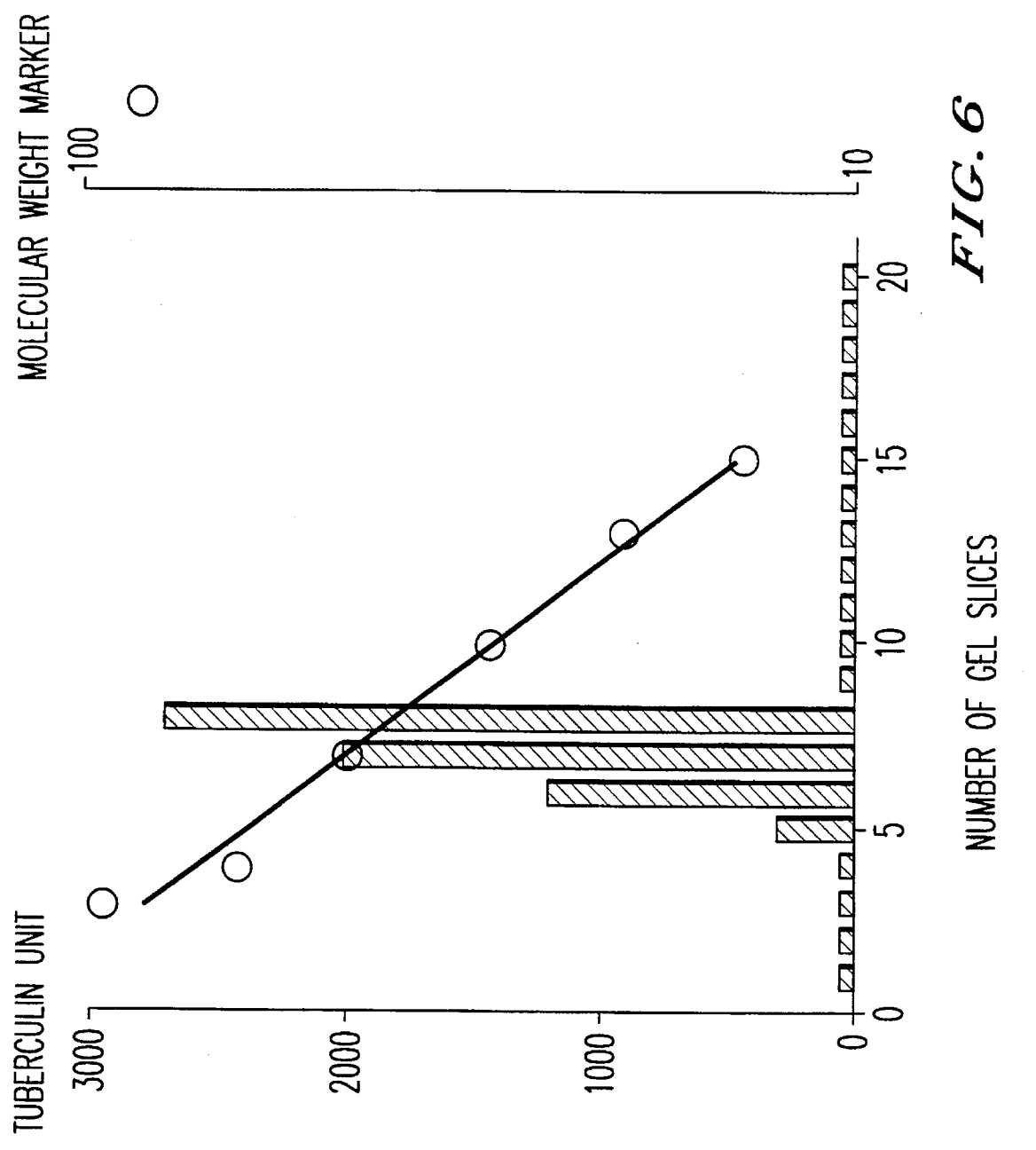

FIG. 6 represents the results of determination of the molecular weight of the molecule capable of showing a HSR reactivity in guinea pigs immunized with living bacteria.

Figure 7:
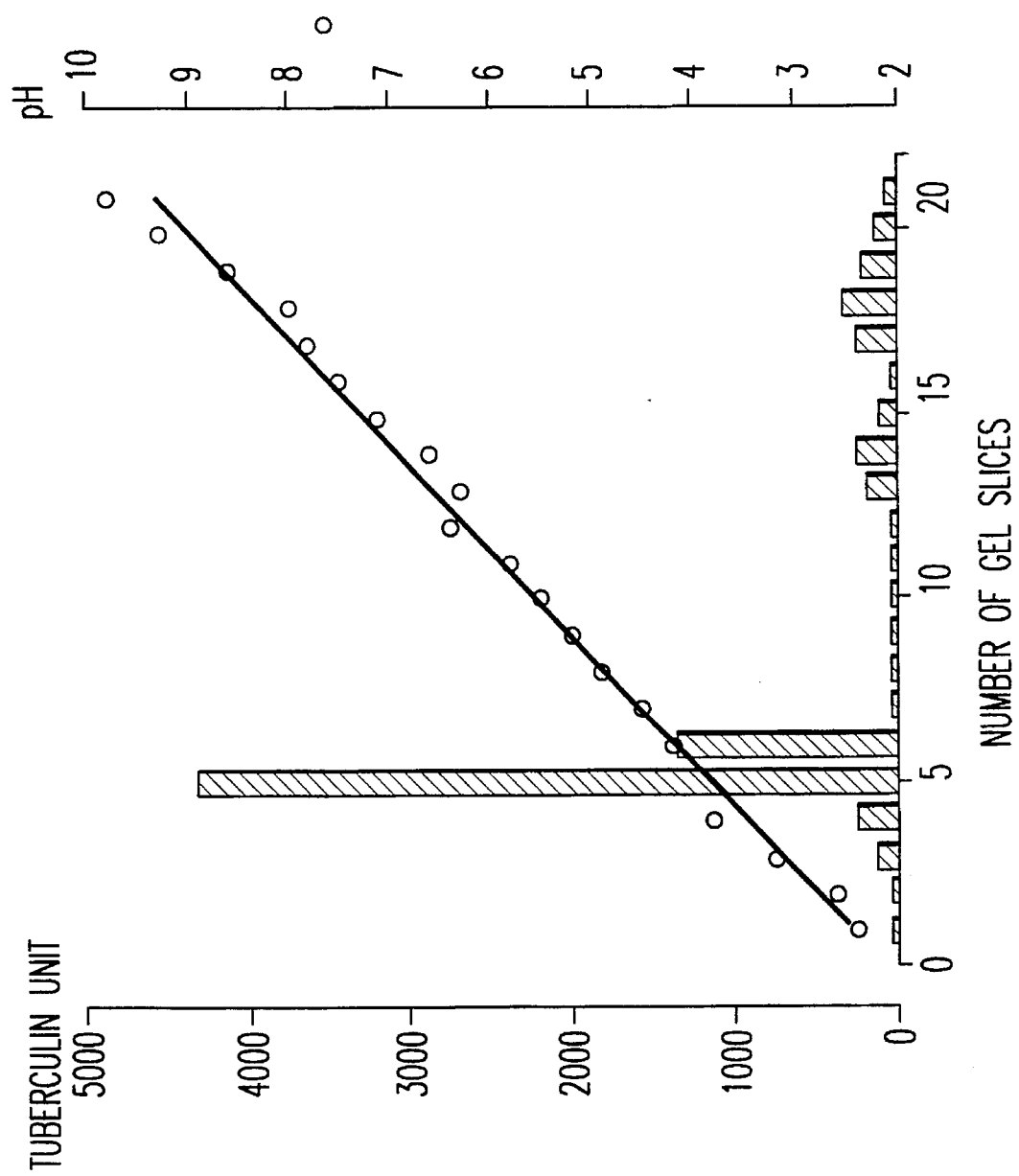

FIG. 7 represents the results of the determination of the isoelectric point of the molecule capable of showing a HSR reactivity in guinea pigs immunized with living bacteria.

EXAMPLES

I - Purification of the LIP-DTH protein

1) Test for monitoring the purification

The purification of the LIP-DTH protein was monitored by measuring delayed-type hypersensitivity reactions (HSR).

A group of 20 female guinea pigs (Hartley albino heterozygote line, weighing 250 to 300 g) was immunized with living BCG or BCG killed by heating.

The living BCG ($2 \times 10^7$ viable units in 0.1 ml of saline solution) one was injected intradermally at 2 sites in the flanks of the animal. 2 mg of BCG killed by heating (120° C., 30 min) were mixed into 0.5 ml of a mixture (1/1) of saline buffer and incomplete Freund's adjuvant (DIFCO) and injected intramuscularly. The sensitized guinea pigs of the two groups were used to test the HSR reactivity between 2 and 10 months after the immunization. Generally, the sensitized guinea pigs were tested 5 or 6 times during this period with an interval of at least one month between two trials.

The HSR reactions were carried out on the flanks of the guinea pigs sensitized and depilated 24 h before injection. Four intradermal injections were made to each flank with the aim of administering to each animal various dilutions of the substance to be tested and various dilutions of a control PPD, so as to obtain a measurement of the level of sensitization of each animal.

Dilutions containing 1, 0.50, 0.25 and 0.125 μg of PPD per 0.1 ml were prepared in a saline solution containing Tween 80 (0.0005%) as described by Laudi et al. (Develop. biol. Standard. 29:393–411). Defined quantities of the substance to be tested were prepared in the same manner in 4 serial dilutions in the same saline solution.

The substance to be tested was administered in 0.1 ml and at different dilutions to 2 to 4 animals which were receiving at the same time different dilutions of the PPD standard having a titre of 40,000 tuberculin units (ITU) per mg.

The reaction was read after 28 hours. The longitudinal and transverse diameters of the erythema were reported in mm. The value of the mean for a given dilution was plotted on a diagram and it was possible to trace a curve using a standard regression analysis. Comparison of the values observed for the standard PPD made it possible to convert the results into conventional tuberculin units (ITU).

2) Culture of the BCG.

The BCG cultures (strain 1173P$_2$) were performed in flasks containing 130 ml of synthetic Sauton medium according to the method described by Gheorghiu et al. (Bull. Inst. Pasteur 81:281–288). The culture medium was harvested after 14 days at 37° C., filtered on a gauze and through a 0.22 μm filter. The medium was carefully washed at 4° C. with deionized water containing butanol (4%) on an MW$_{10}$ Amicon membrane and concentrated about 10-fold. The concentrated medium containing molecules with a molecular weight greater than 10 kDa was freeze-dried and stored at −20° C.

The freeze-dried product has a HSR activity ten times greater in guinea pigs immunized with living bacteria compared with guinea pigs immunized with dead bacteria (FIG. 1).

3) Purification steps. a) filtration on a molecular sieve

A preparative column Si300, 3 μm, 50×750 mm (Serva) was equilibrated with a saline buffer (50 mM Na$_2$HPO$_4$ adjusted to pH 7.5 with KH2PO$_4$) containing butanol (4%). The flow rate of the column was 1.25 ml/min, the maximum pressure of 45 bars was not reached.

The product freeze-dried in the preceding step was dissolved in a buffer/butanol solution at a concentration of 50 mg/ml. It was ultracentrifuged at 40,000 g for 2 hours in order to remove the insoluble residues. After filtration on 0.22 μm filters, aliquot portions (10 ml) containing 500 mg of substance were preserved at −20° C. They were again filtered through a 0.22 μm filter after thawing just before the injection into the column. The optical density profile at 220 nm was recorded (FIG. 2). The six principal fractions harvested as a function of the optical density profile were washed intensively at 4° C. with deionized water containing butanol (4%), concentrated on an MW$_{10}$ membrane and freeze-dried. After freeze-drying, the fractions were weighed and preserved at −20° C. Fraction 4, containing most of the molecules capable of causing a delayed-type hypersensitivity reaction in a guinea pig immunized with living bacteria, was selected and loaded onto the next column (FIG. 2).

The HSR activity of fraction 4 was evaluated at about 75,000 TU per mg in guinea pigs immunized with living bacteria for 14,000 TU per mg in guinea pigs immunized with dead bacteria.

b) ion-exchange chromatography column

A preparative column DEAE-TSK 5PW, 21.5×150 mm (LKB) was equilibrated with a saline buffer of low ionic concentration (10 mM $Na_2HPO_4/NaH_2PO_4$, pH 7.5, and 10 mM NaCl) containing butanol (4%). The controlled flow rate was 6 ml per min with a maximum pressure of 30 bars. A linear gradient of NaCl of 1M maximum in the same buffer was applied after the injection of 100 mg of the preceding fraction 4 obtained from the Si300 column. dissolved in 4 ml of the starting saline buffer. Five predominant fractions were recovered as a function of the optical density (220 nm). They were washed intensively at 4° C. with deionized water/4% butanol, concentrated on an $MW_{10}$ membrane and freeze-dried. Only fraction 1 containing the antigens capable of showing a HSR reaction in the guinea pig immunized with living bacteria was loaded onto the next column.

The HSR activity of fraction 1 was evaluated at 180,000 ITU per mg in guinea pigs immunized with living BCG against 5000 ITU per mg in bacteria immunized with dead BCGs (FIG. 3).

c) reversed-phase chromatography column

A 10 μm $C_8$ RP300 column of 4.6×250 mm (Aquapore Brownlee Lab.) was equilibrated with an ammonium acetate buffer (20 mM $NH_4COOCH_3$, pH 6.5) with a controlled flow rate of 2 ml per minute and a maximum pressure of 115 bars. 7.5 mg of the preceding fraction 1 obtained from the DEAE column was injected into 1 ml of ammonium acetate buffer. An elution gradient containing 0 to 90% acetonitrile for the highest concentrations was established according to the profile represented in FIG. 4. The optical density profile at 220 nm made it possible to isolate 6 major fractions which were concentrated under vacuum at 40° C. in order to remove the acetonitrile, and freeze-dried.

The fraction 3 corresponding to 20–22% acetonitrile presented a very high HSR activity in guinea pigs immunized with living BeG (about 550,000 ITU/mg) and a very low activity in guinea pigs immunized with dead BCG (less than 3000 ITU/mg) (FIG. 4).

Fraction 3 was retitrated more precisely using 8 guinea pigs per immunization group.

The purified substance was 100 times more active in guinea pigs immunized with living bacteria compared with guinea pigs immunized with dead bacteria. The activity was 415,000 ITU/mg and 3000 ITU/mg respectively after a precise measurement of the titre (FIG. 5).

II - Characteristics of the LIP-DTH protein

1) Composition of the LIP-DTH protein

The overall composition of carbohydrates and amino acids present in the purified fraction indicates that about 20% of the total mass is composed of various major monosaccharides (mannose, galactose, arabinose and xylose).

This protein is sensitive to proteolytic enzymes such as pronase and subtilopeptidase, which means that its biological activity disappears after incubation in the presence of these enzymes under the usual buffer and concentration conditions.

Analysis of the $NH_2$-terminal sequence of the protein revealed the following peptide sequence (SEQ ID NO:1): Thr-pro-pro-$X_1$-Glu-$X_2$-Pro-Pro-Pro-Pro-Gln-$X_3$-Val-$X_4$-Leu in which $X_1$, $X_2$, $X_3$ and $X_4$ represent modified amino acids.

2) Determination of the molecular weight

The molecular weight was studied on SDS-PAGE containing 10% acrylamide; the gel of about 10 cm for the separating part, was harvested and cut into fragments 0.5 cm in length. Each gel fragment was eluted in 1 ml of water in the presence of 0.0005% Tween 80, then the HSR activity was tested on guinea pigs immunized with living bacteria. The front and the maximum activity were found in a region of 45 kDa (FIG. 6).

This molecular weight determination is performed with an approximation of about 10%, an approximation which can be ascribed to the variations of the results as a function of the calibration kits used. (Pharmacia for example).

3) Determination of the isoelectric point

The isoelectric point was determined on a polyacrylamide gel including ampholytes (Servalyt 2–11). The gel after isoelectric focusing of an aliquot of the LIP-DTH fraction in an electric field based on conventional conditions was cut into 21 fragments of 0.5 cm. Each gel fragment was eluted in 1 ml of water in the presence of 0.0005% Tween 80; the pH was measured, then the HSR activity was tested on guinea pigs immunized with living bacilli. The main activity, about 4000 ITU per ml is found for a pH of 4±0.2, the low activity in the pH 8 region corresponding to the position of the deposition of the molecules to be analysed, hence the small residual activity visible in FIG. 7.

4) Toxicity

Tests of toxicity were carried out in guinea pigs according to the Codex recommendations for a purified tuberculin.

Acute toxicity: after injection of the equivalent of 50,000 ITU of LIP-DTH protein, no toxicity was observed.

Sensitization: a test of non-sensitization consisting of injecting 4 times in 1 month a dose corresponding to 500 ITU of purified protein showed an absence of toxicity under semichronic conditions and the absence of sensitization.

Moreover, mice received doses of between 1 ITU and 2000 ITU without presenting clinical disorders. Likewise, squirrel monkeys (12) received doses of 200 ITU intradermally without presenting local or general signs.

---

SEQUENCE LISTING ( 1 ) GENERAL INFORMATION:

( i i i ) NUMBER OF SEQUENCES: 1

-continued ( 2 ) INFORMATION FOR SEQ ID NO:1:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 4

( i x ) FEATURE:
( A ) NAME/KEY: Modified-site
( B ) LOCATION: 6

( i x ) FEATURE:
( A ) NAME/KEY: Modified-site
( B ) LOCATION: 12

( i x ) FEATURE:
( A ) NAME/KEY: Modified-site
( B ) LOCATION: 14

( x i ) SEQUENCE DESCRIPTION: SEQ ID NO:1:

Thr Pro Pro Xaa Glu Xaa Pro Pro Pro Pro Gln Xaa Val Xaa Leu
1 5 10 15

What is claimed is:

1. A peptide or protein having an $NH_2$-terminal sequence of SEQ ID NO: 1 wherein the peptide or protein sequence is capable of initiating delayed hypersensitivity reactions of different intensity in the presence of living bacteria as opposed to dead bacteria of the *Mycobacterium tuberculosis* complex and is further characterized in that it contains no more than 0.5% by weight of amino acids tyrosine, phenylalanine, methionine, histidine, arginine and cysteine.

2. The protein according to claim 1, said protein being obtained from BCG culture supernatant by the purification steps consisting of:

(a) filtration on molecular sieve;

(b) ion-exchange chromatography on DEAE; and ( c ) reversed-phase chromatography.

3. The protein according to claim 2, wherein step (a) is filtration on a 3 μM Si 300 column equilibrated with a $Na_2HPO_4/KH_2PO_4$ buffer, pH 7.5, and elution with said buffer at a flow rate of 1.25 ml/min under a pressure of less than 45 bars.

4. The protein according to claim 1, wherein step (b) is ion-exchange chromatography on a DEAE-TSK 5PW column equilibrated with a 10 mM $NA_2HPO_4/NaH_2PO_4$ buffer, pH 7.5, 10 mM NaCl gradient from 0 to 1M in said buffer, and a linear NaCl gradient from 0 to 1M in said buffer with a flow rate of 6 ml/min under a pressure of less than 30 bars.

5. The protein according to claims 2, wherein step (c) is reversed-phase ion-exchange chromatography on a 10 μM $C_8$ RP 300 column equilibrated with an $NH_4COOH_3$ buffer, pH 6.5, and elution with a 0 to 90% acetonitrile gradient in said buffer with a flow rate of 2 ml/min and under a pressure of less than 115 bars.

6. The protein according to claim 1, said protein having an apparent molecular weight of about 45 KDa in a polyacrylamide gel in the presence of SDS.

7. The protein according to claim 1, said protein having an isoelectric point of 4±0.2.

8. A diagnostic composition comprising the protein according to claim 1.

9. The composition according to claim 8, for the in vivo diagnosis of an infection by bacteria of the *Mycobacterium tuberculosis* complex, comprising in addition, an excipient containing a surface-active agent.

10. An immunogenic composition, comprising the protein according to claim 1.

11. An immunogenic composition, comprising the protein according to claim 1 as carrier protein onto which is added or attached an epitope towards which a T lymphocyte response is sought.

12. A process for the detection of a T lymphocyte response against an infectious agent in a host, comprising the following steps:

culturing in an artificial medium mononuclear cells of the host containing varying concentrations of the peptide or of the protein, as defined in claim 1, and detecting activation of the mononuclear cells of the host.

13. The process according to claim 12, wherein the detection of the activation of the cells is carried out by a method selected from the group consisting of: direct observation of the cells under a microscope, incorporation of radioactive precursors, detection in the culture medium of cytokines and appearance of cytokine receptors at the surface of the cells.

14. The process according to claim 12, wherein the detection of the activation of the cells is carried out by the detection of γ-interferon liberated by the cells by means of an enzymatic immunoassay using a monoclonal antibody.

15. A diagnostic kit for the detection of a T cell response against an infectious agent, comprising:

a culture medium for mononuclear cells, containing varying concentrations of the peptide or of the protein as defined in claim 1, and means for detecting activation of the mononuclear cells of the host.

* * * * *